United States Patent [19]
Gollobin et al.

[11] Patent Number: 5,370,226
[45] Date of Patent: Dec. 6, 1994

[54] DISPOSABLE NEEDLE COVER

[76] Inventors: Peter Gollobin, 54 Woodland Dr., Oyster Bay Cove, N.Y. 11771; Vincent J. Chimienti, 2 Osborne La., Greenvale, N.Y. 11548

[21] Appl. No.: 74,055

[22] Filed: Jun. 9, 1993

[51] Int. Cl.⁵ .............................. B65D 85/20
[52] U.S. Cl. ........................ 206/365; 206/480; 220/4.23
[58] Field of Search ............ 206/363, 364, 365, 366, 206/477, 480, 564, 565; 220/4.21, 4.22, 4.23, 4.24, 4.25, 908; 604/187; 128/DIG. 26

[56] References Cited

U.S. PATENT DOCUMENTS

| | | | |
|---|---|---|---|
| 3,944,069 | 3/1976 | Eldridge, Jr. | 206/365 X |
| 4,875,896 | 10/1989 | Kurtz | 128/DIG. 26 X |
| 5,024,326 | 6/1991 | Sandel et al. | 206/365 X |
| 5,090,564 | 2/1992 | Chimienti | |
| 5,156,267 | 10/1992 | Yates, Jr. et al. | 206/365 X |

Primary Examiner—Paul T. Sewell
Assistant Examiner—Jacob K. Ackun, Jr.
Attorney, Agent, or Firm—Galgano & Burke

[57] ABSTRACT

A disposable needle cover for receiving, containing and disposing of a hypodermic needle with a needle hub. The needle cover includes a needle receptacle having two substantially similar plates pivotally coupled to each other along a pivot axis. The plates are positionable between an open position for receiving the needle and a closed position. A needle container is formed within the plates and positioned, so that placement of the needle into the container pivots the plates into the closed position for containing and disposing of the needle.

21 Claims, 2 Drawing Sheets

DISPOSABLE NEEDLE COVER

BACKGROUND OF THE INVENTION

1. Field of the Invention

The present invention relates to a disposable needle cover for protecting and facilitating safe disposal of a hypodermic needle. More particularly, it relates to a disposable needle cover that allows a hypodermic needle to be safely removed from a syringe and disposed of.

2. The Prior Art

Various types of syringe assemblies for receiving and dispensing medications, as well as other materials have been known. In general, the medications or other materials are introduced into the hollow barrel portion either by receiving the same through the needle which communicates with the barrel interior, or by means of a protective container, such as an ampule, which is placed within the hollow barrel. Applying pressure to the plunger causes the medication or other material to be expressed through the hollow needle.

These various assemblies are often used for patients suffering from infectious diseases. Therefore, it has been considered of great importance in the art to avoid accidents, where doctors, nurses or other persons suffer accidental puncture wounds from used needles. Presently, the safe disposal of used syringes and needles is considered a serious problem in the art, particularly in light of the recent spread of Acquired Immune Deficiency Syndrome (AIDS) and hepatitis, and the widespread abuse of syringes and needles by addicts for administering illicit drugs.

In order to prevent the incidents of puncture wounds which are sometimes accidentally self-inflicted by doctors, nurses and hospital housekeeping staff, there has been a need to provide a simple method for immediately covering a hypodermic needle after use.

One such attempt is set forth in U.S. Pat. No. 5,090,564. This patent discloses a protective container for a needle. However, this patent has certain drawbacks, in that the protective container must be manually moved from the open position into the closed position. A further drawback exists in that since the needle receiving grooves are centrally disposed along each container half, placement of the needle within the grooves does not cause the container to be closed around the needle.

Therefore, it would be advantageous to provide a disposable needle cover, where placement of the needle into the cover causes the cover to move toward the closed position. Furthermore, it would be desirable to have a needle cover that is biased into the closed position once the cover has been pivoted partially toward the closed position.

SUMMARY OF THE INVENTION

Accordingly, it is an object of the present invention to provide a disposable needle cover that overcomes the drawbacks of the prior art and easily collapses around a needle.

It is a further object of the present invention to provide a disposable needle cover, wherein placement of the needle into the needle cover pivots the needle cover into the closed position.

It is a further object of the present invention to provide a disposable needle cover, wherein the needle cover is biased into the closed position, once the needle cover has been partially closed.

These and other related objects according to the invention are achieved by a disposable needle cover or disposable needle trap for receiving, containing and disposing of a used hypodermic needle with a needle hub. The needle trap includes a needle container having a first plate with a first longitudinally extending edge and a second plate with a second longitudinally extending edge. The first and second plates are pivotally coupled together along the first and second longitudinal edges about a pivot axis. The plates are positionable between an open position for receiving the needle and a closed position, wherein the plates lie substantially flat against each other. The needle trap includes means for biasing the first and second plates into the closed position, once the plates have been pivoted partially toward the closed position. A semi-cylindrical tube formed within each of the plates and positioned so that both plates form a cylindrical needle receiving tube in the closed position of the plates for containing the needle. Needle retention means are disposed within the needle receiving tube for engaging and preventing rotation of the needle. The needle trap further includes means for locking the plates into closed position for disposal of the needle trap and needle contained therein.

The cylindrical needle receiving tube is disposed adjacent the pivot axis, so that placement of the needle into either semi-cylindrical tube pivots the plates into a partially closed position. The needle receiving tube has a tube axis and the needle retention means comprise a radially extending finger formed on each of the semi-cylindrical tubes for contacting the needle hub. The biasing means comprises a U-shaped clip having two legs and a bridge member joined between the legs, each leg has an end farthest from the bridge member that is connected to one of the first and second plates. The biasing means alternately comprises two U-shaped clips axially disposed on either side of the fingers.

The locking means comprises a locking tab disposed on one of the first and second plates and a correspondingly shaped locking groove disposed on the other of the first and second plates for receiving a locking tab when the plates are in the closed position. The locking means alternately comprise at least two locking tabs and at least two correspondingly shaped locking grooves. The locking tabs and locking grooves are disposed equidistantly from the pivot axis. The first and second plates, the needle receiving tube, the radially-extending fingers, the U-shaped clips and the locking tabs are integrally formed from plastic, for example.

In a further embodiment of the invention a disposable needle cover is provided for receiving, containing and disposing of a used hypodermic needle with a needle hub. The needle cover includes a needle receptacle, having a first plate and a second plate, pivotally coupled along a pivot axis. The plates are positionable between an open position for receiving the needle and a closed position. A needle container is formed within the plates and positioned so that placement of the needle into the container pivots the plates into the closed position for containing and disposing of the needle.

The needle container is parallel and adjacent to the needle receptacle pivot axis. The disposable needle cover further includes needle retention means disposed within the needle container for engaging and preventing rotation of the needle. The disposable needle cover also includes means for selectively biasing the plates into the open and closed positions dependent upon the relative position of the plates to each other. The disposable needle cover also has means for locking the plates together in a closed position for disposal of the needle cover with the needle contained therein.

A method for securing a hypodermic needle, screwed onto a syringe, within a disposable needle cover includes the steps of providing a needle receptacle and placing the needle into the receptacle parallel and in close proximity to the needle receptacle pivot axis. The needle includes a needle hub and the needle receptacle includes a needle hub bore which are aligned. The needle pivots the plates closed and the plates are subsequently locked. The syringe is unscrewed from the needle and the needle receptacle and needle are disposed of. The needle covers may be packaged in upright semi-closed, ready-to-use containers.

BRIEF DESCRIPTION OF THE DRAWINGS

Other objects and features of the present invention will become apparent from the following detailed description considered in connection with the accompanying drawing which disclose an embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
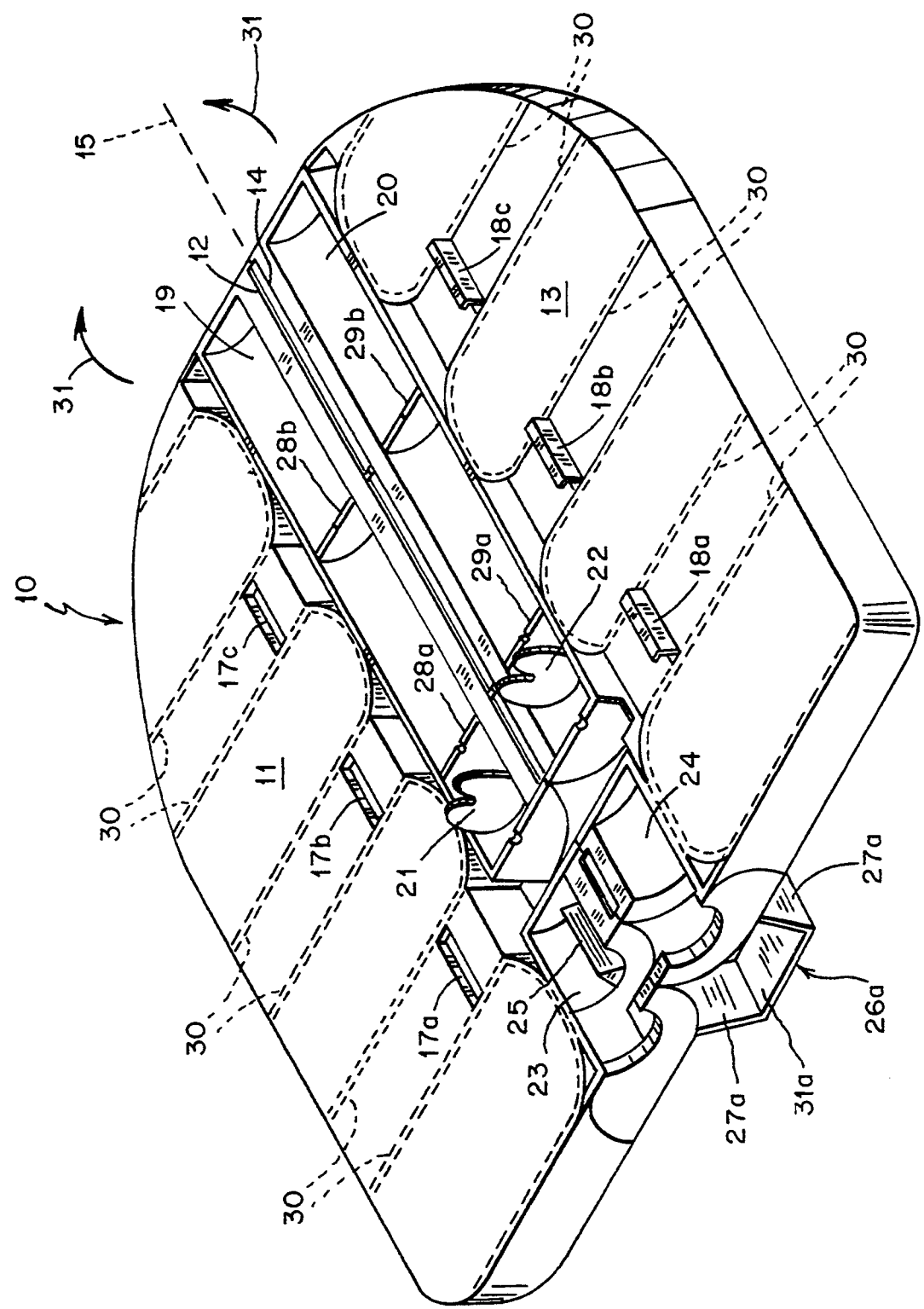
FIG. 1 is a perspective view of an embodiment of the disposable needle cover, shown in the open position.

Referring now in detail to the drawings and in particular FIG. 1, there is shown a disposable needle cover or trap 10 of unitary structure having a first plate 11 with a first longitudinally extending edge 12 and a second plate 13 with a second longitudinally extending edge 14. Plates 11 and 13 are substantially symmetrical and are pivotally coupled to each other along longitudinally extending edges 12 and 14 about a pivot axis 15. First plate 11 includes a set of locking grooves 17a, 17b and 17c for receiving a set of locking tabs or clips 18a, 18b and 18c disposed on second plate 13. First plate 11 includes a first semi-cylindrical shaped tube 19 and second plate 13 includes a second semi-cylindrical shaped tube 20. Semi-cylindrical tubes 19 and 20 form a cylindrical liquid holding compartment that is parallel and adjacent to pivot axis 15 when disposable needle cover 10 is in the closed position. The liquid holding compartment forms a sealed container around the needle point to hold blood or other liquid that may be expelled from the syringe. For example, when performing arterial blood gas tests, blood is expelled from the syringe to remove the trapped air. The liquid holding compartment also has particular application in nuclear medicine, where the liquid in the syringe is radioactive. Needle cover 10 will contain the liquid until proper disposal can be made. One or more partitions 28 and 29 may divide semi-cylindrical tubes 19 and 20 and clamp onto the needle.

First semi-cylindrical tube 19 includes a first circular retention member 21 and second semi-cylindrical tube 20 includes a second circular retention member 22, for example. In the closed position, the needle is held within the V-shaped cutout of retention members 21 and 22. Retention member 21 is slightly offset from retention member 22 axially along pivot axis 15 so that they slide past each other, as needle cover 10 is pivoted into the closed position. Additional retention members are optionally located at spaced intervals along the length of tubes 19 and 20. A first needle hub receiving port or bore 23 is aligned with first semi-cylindrical tube 19. A second needle hub receiving port or bore 24 is aligned with second semi-cylindrical tube 20. A radially extending finger 25 is disposed within first needle hub receiving port 23. A corresponding radially-extending finger may be disposed within second needle hub receiving port 24. The entire needle cover 10 may be manufactured in a single step by injection molding or stamping.

Figure 2:
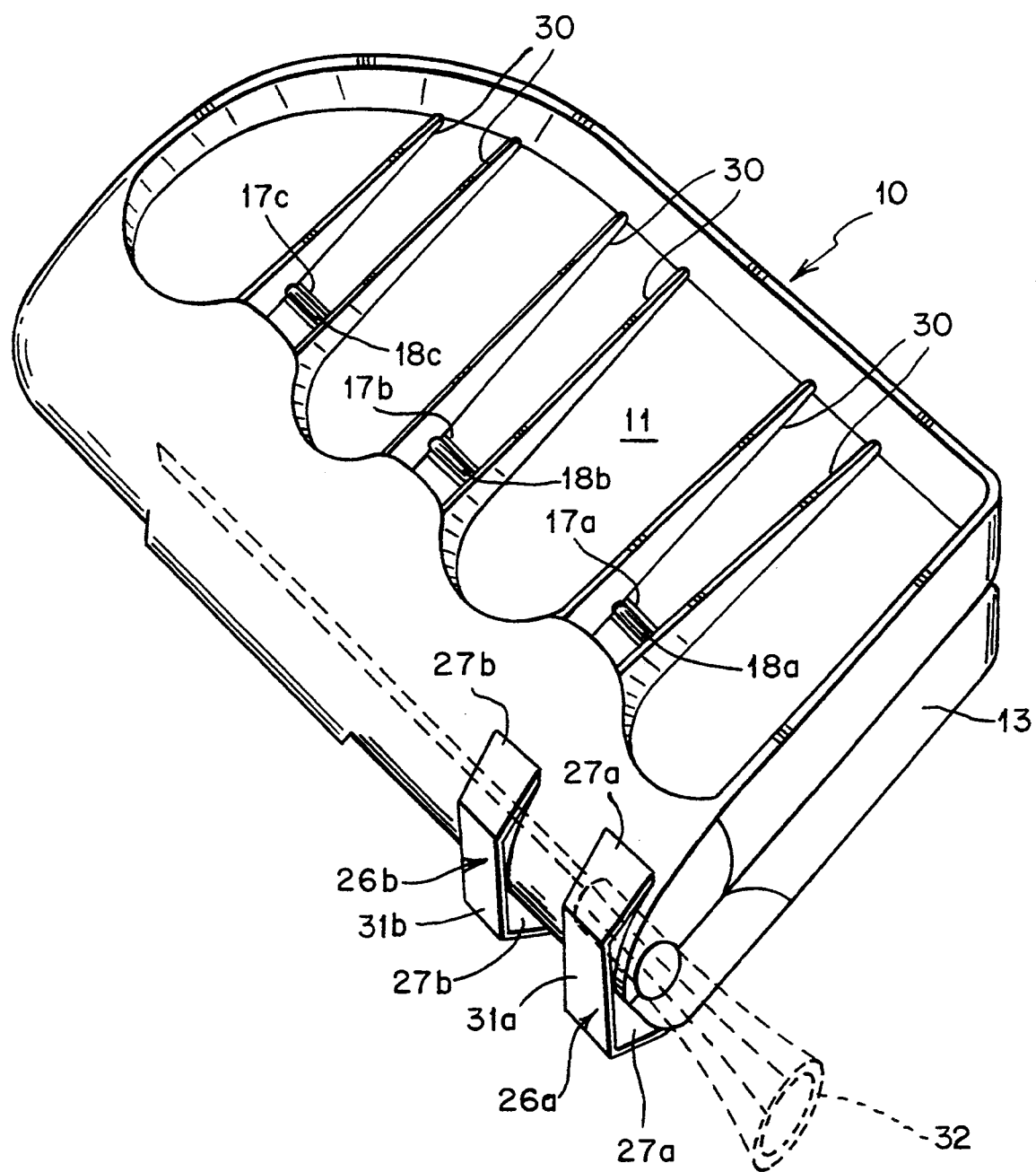
FIG. 2 is a perspective view of the disposable needle cover in the closed position, containing a needle.

As can be seen in FIGS. 1 and 2, U-shaped locking clips 26a and 26b are axially located on either side of needle hub receiving ports 23 and 24. Clips 26 are thin flexible bands or strips having legs 27 joined by bridge members 31 and integrally formed with plates 11 and 13. Disposable needle cover 10 is biased into the open position, as seen in FIG. 1, by clips 26. As disposable needle cover 10 is pivoted into the closed position, legs 27 of clips 26 are forced open. Once plates 11 and 13 are partially closed, for example, are disposed at 90° to each other, clips 26 bias said plates toward each other under the restoring force of said clips. When plates 11 and 13 are together, locking tabs or clips 18 pass through grooves 17 and releasably or non-releasably lock against the outer surface of plate 11, as can be seen in FIG. 2. A set of reinforcing ribs 30 are disposed along the exterior of plates 11 and 13. Ribs 30 are oriented perpendicular to pivot axis 15, for example.

In use, disposable needle cover 10 is held in the palm of the healthcare provider, in the open position, as can be seen in FIG. 1. Alternatively, needle cover 10 may be placed on a flat surface, for example a table top. After use of a hypodermic needle and syringe assembly, the needle is placed into one of semi-cylindrical tubes 19 or 20 in close proximity to pivot axis 15 with the needle hub being aligned with the corresponding needle hub receiving bores 23 or 24. The needle is oriented generally parallel to pivot axis 15. Downward force of the needle into needle cover 10, causes plates 11 and 13 to pivot or collapse along pivot axis 15, i.e. pivot in direction 31. Initially, the downward force must be sufficient to overcome the force necessary to stretch legs 27 of clips 26. Once plates 11 and 13 have moved partially closed, i.e. are disposed at approximately 90° to each other, the restoring force of clips 27 pivots plates 11 and 13 closed. The healthcare provider then simply pushes plates 11 and 13 together so that locking tabs or clips 18 engage grooves 17. With fingers 25 engaging the needle hub, the syringe can be unscrewed from needle 32, as can be seen in FIG. 2. Disposable needle cover 10, having needle 32 safely contained therein, renders said needle harmless to the healthcare provider as well as the patient. Disposable needle cover 10 and needle 32 can then be easily disposed of at the convenience of the healthcare provider.

Alternatively, needle cover 10 is factory packaged in boxes with racks that hold needle cover 10 in an upright semi-closed position, i.e. resting on bridge member 31. The needle is passed down into the upwardly facing groove with the needle hub opening plates 11 and 13 sufficiently so that the needle slides past clips 18 and into the cutouts of retention members 21 and 22. Ideally, plates 11 and 13 are opened enough, so that the cutouts of retention members 21 and 22 open upwardly but the borders below the cutouts are overlapping, so that the needle cannot overshoot its intended location within both cutouts. After the needle hub reaches needle hub receiving bores 23 and 24, plates 11 and 13 are biased back into a closed position around the needle and needle hub. The syringe can subsequently be used as a handle to pull needle cover 10 from the rack. Needle cover 10, with the needle contained therein, can then be laid flat on a surface, i.e. on plates 11 or 13, and snapped into the locked position with one hand.

While several embodiments of the present invention have been shown and described, it is to be understood that many changes and modifications may be made thereunto without departing from the spirit and scope of the invention as defined in the appended claims.

What is claimed is:

1. A disposable needle trap of unitary structure for receiving, containing and disposing of a hypodermic needle with a needle hub, the needle trap comprising:
   a needle container having a first plate with a first longitudinally extending edge and a second plate with a second longitudinally extending edge;
   said first and second plates being pivotally coupled to each other along said first and second longitudinally extending edges about a pivot axis, said plates being positionable between an open position, in which said plates are disposed generally 180° apart for receiving the needle and a closed position wherein said plates lie substantially flat against each other;
   means for biasing said first and second plates into said closed position once said plates have been pivoted partially from said open position toward said closed position said means for biasing comprising at least one generally U-shaped clip having a pair of ends, one end of which is secured to said first plate and the other end of which is secured to said second plate;
   a semi-cylindrical tube formed within each of said first and second plates and positioned so that both plates form a cylindrical needle-receiving tube in said closed position of said plates for containing the needle; and
   means for locking said plates in said closed position for disposal of the needle trap and needle contained therein.

2. The disposable needle trap according to claim 1, wherein said cylindrical needle-receiving tube is disposed adjacent to said pivot axis so that placement of the needle into either of said semi-cylindrical tubes pivots said plates into said predetermined position.

3. The disposable needle trap according to claim 2, wherein said needle receiving tube has a tube axis and a needle retention means comprising:
   a radially-extending finger formed on each of said semi-cylindrical tubes for contacting the needle hub.

4. The disposable needle trap according to claim 3, wherein said biasing means comprises:
   a U-shaped clip having two legs and a bridge member joined between said legs, each of said legs includes an end farthest from said bridge member that is connected to one of said first and second plates.

5. The disposable needle trap according to claim 4, wherein said biasing means comprises two U-shaped clips axially disposed on either side of said fingers.

6. The disposable needle trap according to claim 5, wherein said locking means comprises:
   a locking tab disposed on one of said first and second plates and a correspondingly shaped locking groove disposes on the other of said first and second plates for receiving said locking tab when said plates are in the closed position.

7. The disposable needle trap according to claim 6, wherein said locking means comprises:
   at least two locking tabs and at least two correspondingly shaped locking grooves.

8. The disposable needle trap according to claim 7, wherein said at least two locking tabs and said at least two correspondingly shaped locking grooves are disposed equidistantly from said pivot axis.

9. The disposable needle trap according to claim 8, wherein said first and second plates, said needle receiving tube, said radially-extending fingers, said U-shaped clips and said at least two locking tabs are integrally formed.

10. The disposable needle trap according to claim 9, further comprising reinforcing ribs integrally formed on said first and second plates.

11. The disposable needle trap according to claim 10, wherein said first and second plates are substantially symmetrical.

12. The disposable needle trap according to claim 11, wherein said U-shaped clips are thin flexible strips.

13. The disposable needle trap according to claim 1 additionally includes needle retention means disposed within said needle receiving tube for engaging and preventing rotation of the needle.

14. A disposable needle cover for receiving, containing and disposing of a hypodermic needle with a needle hub, the needle cover comprising:
   a needle receptacle having a first plate and a second plate pivotally coupled to each other along a pivot axis, said plates being positionable between a open position for receiving the needle in which said plates are disposed generally 180° apart and a closed position in which said plates lie substantially flat against each other;
   a needle container formed within said plates and positioned so that placement of the needle into said container pivots said plates into said closed position for containing and disposing of the needle and;
   means for biasing said first and second plates into said closed position once said plates have been pivoted partially from said open position toward said closed position said means for biasing comprising at least one generally U-shaped clip having a pair of ends, one end of which is secured to said first plate and the other end of which is secured to said second plate.

15. The disposable needle according to claim 14, wherein said semi-cylindrical tubes cooperate to form a sealed needle container for holding liquid that is expelled from the hypodermic needle when said plates are in a closed position.

16. The disposable needle cover according to claim 15, wherein said needle container is parallel and adjacent to said needle receptacle pivot axis.

17. The disposable needle cover according to claim 16, further comprising:

needle retention means disposed within said needle container for engaging and preventing rotation of the needle.

18. The disposable needle cover according to claim 17, further comprising:
means for selectively biasing said plates into the open and closed positions dependent upon the relative position of said plates to each other.

19. The disposable needle cover according to claim 18, further comprising:
means for locking said plates together in said closed position for disposal of the needle cover with the needle contained therein.

20. A disposable needle cover for receiving, containing and disposing of a hypodermic needle with a needle hub, the needle cover comprising:
a needle receptacle having a first plate and a second plate pivotally coupled to each other along a pivot axis, said plates being positionable between an open position for receiving the needle in which said plates are disposed generally 180° apart and a closed position in which said plates lie substantially flat against each other;
a needle container formed within said plates wherein said needle container is a sealed needle container for holding liquid that is expelled from the hypodermic needle; and
means for biasing said first and second plates into said closed position once said plates have been pivoted partially from said open position toward said closed position said means for biasing comprising at least one generally U-shaped clip having a pair of ends, one end of which is secured to said first plate and the other end of which is secured to said second plate.

21. A disposable needle trap of unitary structure for receiving, containing and disposing of a hypodermic needle with a needle hub, the needle trap comprising:
a needle container having a first plate with a first longitudinally extending edge and a second plate with a second longitudinally extending edge;
said first and second plates being pivotally coupled to each other along said first and second longitudinally extending edges about a pivot axis, said plates being positionable between an open position, in which said plates are disposed generally 180° apart for receiving the needle and a closed position wherein said plates lie substantially flat against each other;
means for biasing said first and second plates into said closed position once said plates have been pivoted partially form said open position toward said closed position said biasing means comprising a U-shaped clip having two legs and a bridge member joined between said legs, each of said legs including an end farthest from said bridge member that is connected to one of said first and second plates;
a semi-cylindrical tube formed within each of said first and second plates and positioned so that both plates form a cylindrical needle-receiving tube in said closed position of said plates for containing the needle, said cylindrical needle-receiving tube being disposed adjacent to said pivot axis so that placement of the needle into either of said semi-cylindrical tubes pivots said plates into said predetermined position, said needle receiving tube having a tube axis;
needle retention means disposed within said needle receiving tube for engaging and preventing rotation of the needle, said needle retention means comprising a radially-extending finger formed on each of said semi-cylindrical tubes for contacting the needle hub; and
means for locking said plates in said closed position for disposal of the needle trap and needle contained therein.

* * * * *